United States Patent [19]

Zhdanova et al.

[11] 4,237,228
[45] Dec. 2, 1980

[54] METHOD OF PRODUCING L-ISOLEUCINE USING *BREVIBACTERIUM FLAVUM*

[76] Inventors: Nelli I. Zhdanova, Leningradskoe shosse, 112, korpus 3, kv. 748; Tatyana V. Leonova, ulitsa Svobody, 81, korpus 5, kv. 852; Ljudmila F. Kozyreva, 4 Novopodmoskovny pereulok, 4, kv. 80, all of Moscow, U.S.S.R.

[21] Appl. No.: 917,989

[22] Filed: Jun. 22, 1978

[30] Foreign Application Priority Data

Jun. 29, 1977 [SU] U.S.S.R. ............................ 2501219

[51] Int. Cl.$^3$ ...................... C12P 13/06; C12N 15/00; C12R 1/13
[52] U.S. Cl. ................................. 435/116; 435/172; 435/840
[58] Field of Search ..................... 195/47, 96, 79, 112, 195/29; 435/106, 116, 172, 840

[56] References Cited

U.S. PATENT DOCUMENTS

| | | | |
|---|---|---|---|
| 3,058,888 | 10/1962 | Chibata et al. ......................... | 195/29 |
| 3,231,478 | 1/1966 | Uemura et al. ......................... | 195/29 |
| 3,262,861 | 7/1966 | Kinoshita et al. ...................... | 195/29 |
| 3,502,544 | 3/1970 | Sugiskai et al. ........................ | 195/29 |
| 3,767,529 | 10/1973 | Yoshinaga et al. ..................... | 195/30 |

FOREIGN PATENT DOCUMENTS

| | | | |
|---|---|---|---|
| 51-6237 | 2/1976 | Japan ......................................... | 195/47 |
| 51-21077 | 6/1976 | Japan ......................................... | 195/47 |
| 889187 | 2/1962 | United Kingdom ..................... | 195/30 |

OTHER PUBLICATIONS

Ikeda, et al., "Screening of L-Isoleucine Producers among Ethiomine Resistant Mutants of L-Threonine Producing Bacteria", *Agr. Biol. Chem.,* vol. 40, No. 3, (1976), pp. 511–516.

Kisumi, et al., "Isoleucine Accumulation by Regulatory Mutants of *Serratia Marcescens:* Lack of both Feeback Inhibition and Repression" J. Bact., vol. 110, No. 2, (1972), pp. 761–763.

Shilo, et al., "Production of L-Isoleucine by AHV Resistant Mutants of *Brevibacterium flavum*", *Agr. Biol. Chem.,* vol. 37, No. 9, (1973), pp. 2053–2061.

Kase, et al., "L-Isoleucine Production by Analog-resistant Mutants Derived from Threonine-Producing Strain of *Corgnebacterium glutamicam*", *Agr. Biol. chem.,* vol. 41, No. 1, (1977), pp. 109–116.

*Primary Examiner*—Thomas G. Wiseman
*Attorney, Agent, or Firm*—Fleit & Jacobson

[57] ABSTRACT

A method of producing L-isoleucine which comprises culturing the strain of *Brevibacterium flavum* VNII Genetika 10-89 deposited under the number CMIM B-1507 in a nutrient medium containing sources of nitrogen, carbon, mineral salts and vitamins and under aerobic conditions.

Said strain makes it possible to produce L-isoleucine with a yield of 17 g/l and more.

10 Claims, No Drawings

METHOD OF PRODUCING L-ISOLEUCINE USING *BREVIBACTERIUM FLAVUM*

The present invention relates to microbiological industry and, more specifically, to methods of producing amino acids by using microorganisms; more particularly, the present invention relates to methods of producing L-isoleucine.

L-isoleucine is an essential amino acid which finds extensive use as a component of various nutritive mixtures for medical applications. Furthermore, L-isoleucine is employed as an additive to human meals and animal feeds as well as a reagent in the pharmaceutical and chemical industries.

Known in the art are methods for producing L-isoleucine based on the ability of microorganisms to effect transformation of precursors of synthesis of L-isoleucine such as α-aminobutyric acid, α-hydroxybutyric acid, threonine and the like. In said methods microorganisms are cultured in a medium containing the precursor as well as a source of nitrogen, a carbon source and other components (cf. U.S. Pat. Nos. 3,058,888 3,262,861; 3,231,478; 3,502,544). However, introduction of a precursor into a nutrient medium causes higher production costs of L-isoleucine and hinders its recovery.

Also known in the art are methods of producing L-isoleucine based on a direct fermentation thereof by using mutant strains of such species as *Serratia marcescens, Brevibacterium flavum, Corynebacterium acetoacidophilum, Arthrobacter citreus, Corynebacterium glutamicum*.

Using the given methods L-isoleucine is obtained by culturing said microorganisms in nutrient media containing sources of carbon, nitrogen, mineral salts, growth factors and vitamins. Said culturing is effected in the absence of any precursor of L-isoleucine (cf. J. Bacter 1972, 110, 2,761; U.S. Pat. No. 3,767,529; Japanese Patents Nos. 51-6237; Agr. Biol. Chem. 1976, 40,3, 511; Agr. Biol. Chem., 1977, 41, 1, 109). Mutant strains are derived from wild-type strains when exposed to a mutagenic factor followed by selection by means of analogues of amino acids. A distinctive genetic characteristic of these mutants capable of superproduction of L-isoleucine resides in either their resistance to α-amino-β-hydroxyvaleric acid (analogue of threonine and isoleucine), or in resistance to a combination of two or more analogues of the following aminoacids: threonine, isoleucine, valine, lysine, methionine, or leucine. Such mutant strains produce L-isoleucine with a yield of from 6.7 to 14.7 g/l. However, in said methods a complex-composition nutrient medium is used which contains carbohydrates as the main carbon source (glucose, saccharose, molasses), mineral nitrogen, vitamins, soybean protein hydrolyzates and, in some cases, amino acids.

Therefore, all prior art methods for producing L-isoleucine either necessitate the use of precursors or, in the case of a direct synthesis of L-isoleucine, the product yield is insufficient and nutrient media of a complex composition are employed. Furthermore, for selection of the prior art mutant strains use should be made of a great number of analogues of amino acids.

The present invention aims at providing a method of producing L-isoleucine by a direct fermentation of a producing strain featuring a higher yield of L-isoleucine in nutrient media having a simpler composition.

The present invention is directed to the provision of such a mutant strain of the Brevibacterium species which would give L-isoleucine in a high yield on nutrient medium having a simple composition.

This object is accomplished by a method of producing L-isoleucine by culturing microorganisms *Brevibacterium flavum* in a nutrient medium containing sources of carbon, nitrogen, mineral salts and vitamins under aerobic conditions. In accordance with the present invention use is made of the mutant strain *Brevibacterium flavum* VNII Genetika 10-89. The term VNII Genetika means an abbreviation of the title of the All-Union Research Institute for Genetics and Selection of Industrial Microorganisms. Said strain is a newly-obtained mutant which has been deposited in the Central Museum of Industrial Microorganisms of the Institute VNII Genetika and given the number CMIM B-1507 whence it is available.

Said strain can produce L-isoleucine with a yield of 17 g/l and more. An important advantage of the strain according to the present invention resides in that it is cultured in a simple-composition nutrient media requiring no precursors. Furthermore, this strain is prepared in a more simple and less expensive manner, since only one analogue of L-isoleucine is used for its preparation.

According to the present invention, the method of producing L-isoleucine comprises culturing said strain of *Brevibacterium flavum* VNII Genetika 10-89 in a nutrient medium containing sources of carbon, nitrogen, minerals salts and vitamins.

The strain of *Brevibacterium flavum* VNII Genetika 10-89 is derived from the known strain of *Brevibacterium flavum* 178 which is a producer of L-lysine and differs from the wild-type strain in requiring homoserine. The strain of *Brevibacterium flavum* 178 and the wild-type strain are deposited in the Central Museum of Industrial Microorganism of the Institute VNII Genetika under the numbers CMIM B-1005 and CMIM B-42 respectively.

The strain VNII Genetika 10-89 (CMIM B-1507) is prepared in the following manner. Cells of said strain of *Brevibacterium flavum* 178 requiring homoserine for its growth are cultured for 18 to 20 hours in an agar complete medium and subjected to a mutagenic treatment of vapours of diethylsulphate according to the following procedure. A drop of diethylsulphate (0.05 ml) is placed onto the inner surface of a glass test-tube (with a volume of 20 ml), containing the culture on a slant agar. The test tube is closed with a wadded tap and maintained for 6 hours at a temperature of 30° C. Then the cells are taken off the slant agar surface by means of a loop and are used for the preparation of a suspension in a physiological solution at a concentration of cells of $1 \times 10^8$. The resulting suspension is inoculated on plates with an agar minimal medium containing no homoserine. On expiration of 5 days of incubation at a temperature of 30° C. the grown colonies of revertants are isolated and tested for the ability of to produce L-isoleucine in a liquid nutrient medium containing sources of carbon, nitrogen, mineral salts and vitamins. As a result of such tests a mutant is isolated which has lost its ability to produce lysine but has the ability of accumulating several grams of L-isoleucine. Cells of the thus-isolated mutant in its latest logarithmic phase of growth are exposed to N-methyl-N'-nitro-N-nitrosoguanidine (0.5 mg/ml) over 30 minutes at a temperature of 30° C., whereafter they are inoculated in the amount of $10^6$ on plates with an agar medium containing O-methylthreonine (which is an analogue of L-isoleucine) in a concentration of 5 mg/ml. The colonies grown after 5 days of incubation have been selected as mutants resistant to the inhibiting effect of the analogue and tested for the ability of excreting isoleucine into the liquid nutrient medium. The best mutant producing about 10 g/l of L-isoleucine is selected and its cells, after treatment with N-methyl-N'-nitro-N-nitrosoguanidine following the above-described procedure, are inoculated or agar medium containing 10 mg/ml of O-methylthreonine. The method of isolation of the resistant mutants and tests thereof for the ability of excreting L-isoleucine are similar to those described hereinabove. As a result, a strain is obtained which is designated as VNII Genetika. For the selection of the strain only one analogue of isoleucine has been used. Said strain requires no amino acids for its growth, while retaining the vitamin requirement (of biotin and thiamine) inherent in the wild-type strain of *Brevibacterium flavum*. The strain VNII Genetika 10-89 is deposited in the Central Museum of industrial microorganisms of the Institute VNII Genetika under the number of CMIM B-1507.

Apart from the resistance to O-methylthreonine the morphological characteristics of the strain VNII Genetika 10-89 are identical to those of the known wild-type strains of Brevibacterium flavum (cf. British Pat. No. 889,187, Y. Gen. Appl. Microbid, 1967, 13, 279).

For a better understanding of the present invention some specific Examples illustrating the production of L-isoleucine are given herein below.

EXAMPLE 1

A culture of the strain of *Brevibacterium flavum* VNII Genetika 10-89 is grown for a period of from 24 to 36 hours at a temperature of 30° C. on slant media with a meat-peptone agar. Thereafter it is inoculated, by means of a loop, into 750 ml flasks each containing 100 ml of a seed medium. As the seed medium use is made of a meat-peptone bouillon which is sterilized prior to inoculation. After inoculation the flasks are placed onto a rotatory shaker (220-240 r.p.m.) and the growing of the seed material is effected at a temperature of 30° C. for a period of from 20 to 24 hours. The thus prepared seed material is introduced in an amount of from 3 to 5 vol.% into 750 ml flasks each containing 25 ml of nutrient medium having the following composition:

| | |
|---|---|
| glucose | 130.0 g/l |
| (NH$_4$)$_2$SO$_4$ | 30.0 g/l |
| KH$_2$PO$_4$ | 1.5 g/l |
| MgSO$_4$ | 0.5 g/l |
| CaCO$_3$ | 40.0 g/l |
| biotin | 200.0 mcg/l |
| thiamine | 300.0 mcg/l |
| tap water | to one liter. |

All components of the medium are sterilized under a pressure of 0.5 atm for 30 minutes. After sterilization the medium pH is adjusted to 7.0-7.2 with sulphuric acid.

Culturing is effected under aeration conditions at a temperature of 30° C. for 72 hours till L-isoleucine is is accumulated in the amount of 17.0 g/l.

EXAMPLE 2

Preparation of the seed material is effected in a manner similar to that described in the foregoing Example 1. Culturing is effected as in Example 1 using a nutrient medium of the following composition:

| | |
|---|---|
| glucose | 100.0 g/l |
| (NH$_4$)$_2$SO$_4$ | 30.0 g/l |
| KH$_2$PO$_4$ | 1.5 g/l |
| MgSO$_4$ | 0.5 g/l |
| CaCO$_3$ | 40.0 g/l |
| biotin | 200.0 mcg/l |
| feed concentrate B$_{12}$ | 5 g/l |
| tap water | to one liter. |

On expiration of 66-72 hours of culturing in the culture broth L-isoleucine is accumulated in the amount of 19.0 g/l.

By the term feed concentrate B$_{12}$ is meant a product which is prepared by fermentation of wastes resulting from acetone-butanol fermentation by means of methane-producing bacteria, followed by drying the microbial mass employed as an additive to animal feed.

EXAMPLE 3

Preparation of the seed material is effected in a manner similar to that described in the foregoing Example 1. Culturing is effected as in Example 1 using a nutrient medium of the following composition:

| | |
|---|---|
| saccharose | 130.0 g/l |
| (NH$_4$)$_2$SO$_4$ | 30.0 g/l |
| KH$_2$PO$_4$ | 1.5 g/l |
| MgSO$_4$ | 0.5 g/l |
| CaCO$_3$ | 40.0 g/l |
| thiamine | 300.0 mcg/l |
| desthiobiotin | 500.0 mcg/l |
| tap water | to one liter. |

After 72 hours of culturing L-isoleucine is accumulated in the amount of 17.3 g/l.

EXAMPLE 4

Preparation of the seed material is effected in a manner similar to that described in the foregoing Example 1. Culturing is also effected as in Example 1 using a nutrient medium of the following composition:

| | |
|---|---|
| saccharose | 130.0 g/l |
| (NH$_4$)$_2$SO$_4$ | 30.0 g/l |
| KH$_2$PO$_4$ | 1.5 g/l |
| MgSO$_4$ | 0.5 g/l |
| CaCO$_3$ | 40.0 g/l |
| desthiobiotin | 500.0 mcg/l |
| feed concentrate B$_{12}$ | 5.0 g/l |
| tap water | to one liter. |

After 66-72 hours of the culture growth L-isoleucine is accumulated in the culture liquid in the amount of 17.2 g/l. In the above Examples recovery of L-isoleucine is performed by conventional methods.

What is claimed is:

1. A method of producing L-isoleucine by direct fermentation of a producing strain comprising:
   (A) providing a nutrient medium consisting essentially of sources of carbon, nitrogen, mineral salts, vitamins, and water, with the proviso that precursors of L-isoleucine and amino acids are absent;
   (B) cultivating the strain of Brevibacterium flavum VNII Genetika 10-89 deposited under the number CMIM B-1507 in said medium under aerobic conditions until L-isoleucine is accumulated in an amount of at least 17 grams per liter; and (C) recovering the accumulated L-isoleucine from said medium.

2. The method of claim 1 wherein the strain of *Brevibacterium flavum* VNII Genetika 10-89 is resistant to the inhibiting effect of O-methylthreonine.

3. The method of claim 2 wherein the source of carbon is glucose or sacchrose.

4. The method of claim 3 wherein the vitamins are selected from at least one of the group consisting of biotin, desthiobiotin, thiamine and feed concentrate $B_{12}$.

5. The method of claim 4 wherein the vitamins are biotin and thiamine.

6. The method of claim 4 wherein the vitamins are biotin and feed concentrate $B_{12}$.

7. The method of claim 4 wherein the vitamins are thiamine and desthiobiotin.

8. The method of claim 4 wherein the vitamins are desthiobiotin and feed concentrate $B_{12}$.

9. The method of claim 4 wherein the nitrogen source is $(NH_4)_2SO_4$.

10. The method of claim 9 wherein the mineral salts are $KH_2PO_4$, $MgSO_4$ and $CaCO_3$.

* * * * *